US010395346B2

(12) United States Patent
Lee et al.

(10) Patent No.: US 10,395,346 B2
(45) Date of Patent: Aug. 27, 2019

(54) ULTRASONIC APPARATUS AND METHOD FOR CONTROLLING THE SAME

(71) Applicant: SAMSUNG MEDISON CO., LTD., Hongcheon-gun, Gangwon-do (KR)

(72) Inventors: Jae Sung Lee, Incheon (KR); Hak-Il Kang, Yongin-si (KR); Sung-Ah Park, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 48 days.

(21) Appl. No.: 15/093,530

(22) Filed: Apr. 7, 2016

(65) Prior Publication Data
US 2017/0109869 A1    Apr. 20, 2017

Related U.S. Application Data

(60) Provisional application No. 62/243,380, filed on Oct. 19, 2015.

(30) Foreign Application Priority Data

Nov. 30, 2015   (KR) .................. 10-2015-0168351

(51) Int. Cl.
*G09G 5/00* (2006.01)
*G06T 5/00* (2006.01)
(Continued)

(52) U.S. Cl.
CPC ............ *G06T 5/003* (2013.01); *A61B 8/4405* (2013.01); *A61B 8/4444* (2013.01); *A61B 8/461* (2013.01);
(Continued)

(58) Field of Classification Search
CPC .. G06T 5/003; G06T 3/40; G06T 7/00; G06T 2200/24; G06T 2207/10016;
(Continued)

(56) References Cited

U.S. PATENT DOCUMENTS

| 2008/0146931 | A1* | 6/2008 | Zhang ................ G01S 15/8995 600/447 |
| 2008/0215982 | A1* | 9/2008 | Washburn .............. A61B 8/08 715/722 |
| 2014/0088423 | A1* | 3/2014 | Noguchi ............. A61B 8/0891 600/440 |

FOREIGN PATENT DOCUMENTS

| EP | 2716232 A1 | 4/2014 |
| JP | 2000-005179 A | 1/2000 |

(Continued)

OTHER PUBLICATIONS

Extended European Search Report dated Feb. 28, 2017 issued in European Patent Application No. 16164266.5.

*Primary Examiner* — Insa Sadio
(74) *Attorney, Agent, or Firm* — Morgan, Lewis & Bockius LLP

(57) ABSTRACT

Disclosed herein are an ultrasonic apparatus, which substitutes a frame image having a large motion blur factor and being currently displayed with a frame image having a small motion blur factor and obtained prior to a select instruction input time to display the substituted image when a select instruction for selecting the frame image being displayed or a substitute image display instruction is input, and a method for controlling the same. The ultrasonic apparatus includes an image processor to generate a plurality of frame images based on ultrasonic signals, a display to sequentially display the plurality of frame images, an input device to receive a select instruction for selecting a frame image being displayed on the display among the plurality of frame images; and a controller to control the display to display at least one of frame images, each of which has a motion blur factor equal to or less than a predetermined threshold value and is obtained prior to the select instruction input time, among the plurality of frame images when a motion blur factor of the (Continued)

frame image selected by the select instruction exceeds the threshold value or a substitute image display instruction is input.

18 Claims, 12 Drawing Sheets

(51) Int. Cl.
  *G06T 3/40* (2006.01)
  *A61B 8/08* (2006.01)
  *A61B 8/00* (2006.01)
  *G06T 7/13* (2017.01)

(52) U.S. Cl.
  CPC .............. *A61B 8/463* (2013.01); *A61B 8/467* (2013.01); *A61B 8/5276* (2013.01); *G06T 3/40* (2013.01); *G06T 7/13* (2017.01); *A61B 8/085* (2013.01); *A61B 8/464* (2013.01); *G06T 2200/24* (2013.01); *G06T 2207/10016* (2013.01); *G06T 2207/10132* (2013.01)

(58) Field of Classification Search
  CPC ... G06T 2207/10132; G06T 7/13; A61B 8/08; A61B 8/085; A61B 8/4405; A61B 8/4444; A61B 8/461; A61B 8/463; A61B 8/464; A61B 8/467; A61B 8/5276
  USPC ................................ 345/156; 600/443, 440
  See application file for complete search history.

(56) References Cited

FOREIGN PATENT DOCUMENTS

| | | |
|---|---|---|
| JP | 2010-233956 A | 10/2010 |
| WO | 03/047433 A2 | 6/2003 |

\* cited by examiner

ULTRASONIC APPARATUS AND METHOD FOR CONTROLLING THE SAME

CROSS-REFERENCE TO RELATED APPLICATION

This application claims the benefit of U.S. Provisional Application No. 62/243,380, filed on Oct. 19, 2015 in the USPTO and Korean Patent Application No. 10-2015-0168351, filed on Nov. 30, 2015 in the Korean Intellectual Property Office, the disclosure of which is incorporated herein by reference.

BACKGROUND

1. Field

Embodiments of the present disclosure relate to an ultrasonic apparatus for imaging ultrasonic signals to provide ultrasonic images to a user and a method for controlling the same.

2. Description of the Related Art

An ultrasonic apparatus transmits ultrasonic waves from a body surface of a target object toward a predetermined portion inside a body, and uses information of ultrasonic echoes reflected from tissues inside the body to noninvasively obtain tomographic images of soft tissues or blood flow.

The ultrasonic apparatus has advantages of a compact size, an inexpensive cost, enabling an image display of a target object in real time, and a high safety not causing exposure to radiation including X-rays and the like. With such advantages, an ultrasonic diagnosis apparatus has been widely used for diagnosing cardiac, breast, abdominal, urinary, and gynecological diseases.

The ultrasonic apparatus may display ultrasonic images in real time based on ultrasonic waves (ultrasonic echoes) reflected from a target object. If an ultrasonic image being currently displayed contains information of an anatomical position of a target object to be diagnosed, a user may input a select instruction for the ultrasonic image. Once the select instruction is input, an ultrasonic apparatus may freeze the ultrasonic image being displayed in real time to provide continuously the user with the ultrasonic image being currently displayed.

SUMMARY

Embodiments disclosed herein are to provide an ultrasonic apparatus, which substitutes a frame image having a large motion blur factor and being currently displayed with a frame image having a small motion blur factor and obtained prior to a select instruction input time to display the substituted image when a select instruction for selecting the frame image being displayed or a substitute image display instruction is input, and a method for controlling the same.

In accordance with one embodiment of the present disclosure, an ultrasonic apparatus includes an image processor to generate a plurality of frame images based on ultrasonic signals, a display to sequentially display the plurality of frame images, an input device to receive a select instruction for selecting a frame image being displayed on the display among the plurality of frame images, and a controller to control the display to display at least one of frame images, each of which has a motion blur factor equal to or less than a predetermined threshold value and is obtained prior to a select instruction input time, among the plurality of frame images when a motion blur factor of the frame image selected by the select instruction exceeds the threshold value or a substitute image display instruction is input.

Also, the controller may calculate a motion blur factor of an $N^{th}$ frame image based on a difference between the $N^{th}$ frame image (N is a natural number equal to or greater than 2) and an $N-1^{th}$ frame image, which is a previous frame image of the $N^{th}$ frame image, among the plurality of frame images.

Further, the controller may control the display to display a frame image closest to the selected frame image among the frame images, each of which has the motion blur factor equal to or less than the threshold value and is obtained prior to the select instruction input time.

Furthermore, the controller may control the display to display at least one frame image obtained during a time period in which a plurality of successive frame images, each of which has a motion blur factor equal to or less than the threshold value, are obtained prior to the select instruction input time, when the time period exceeds a predetermined threshold time.

Moreover, the controller may control the display to display a frame image having a minimum motion blur factor among the plurality of successive frame images obtained during the time period.

Also, the controller may control the display to display simultaneously multiple frame images selected based on the motion blur factors among the plurality of successive frame images obtained during the time period.

Further, the display may display the motion blur factors of the multiple frame images being simultaneously displayed in association with the multiple frame images.

Furthermore, the input device may receive a select instruction for selecting one among the multiple frame images being simultaneously displayed.

Moreover, the controller may control the display to magnify and display a selected frame image when the select instruction is input to select one among the multiple frame images being simultaneously displayed.

Also, the controller may control the display to display information related to a motion blur factor of the selected frame image when the motion blur factor of the selected frame image exceeds the threshold value.

Moreover, the ultrasonic apparatus may further include a speaker to output information related to the ultrasonic apparatus as a sound, and the controller may control the speaker to output information related to a motion blur factor of the selected frame image as a sound when the motion blur factor of the selected frame image exceeds the threshold value.

Furthermore, the ultrasonic apparatus may further include an ultrasonic probe to obtain the ultrasonic signals containing information of a target object in real time, and the image processor may generate the plurality of frame images in real time based on the ultrasonic signals obtained in real time.

Also, the ultrasonic apparatus may further include a storage device to store at least one among the plurality of frame images generated in real time.

Further, the controller may control the storage device to store frame images, each of which has a motion blur factor equal to or less than the threshold value, among the plurality of frame images generated in real time.

In accordance with one embodiment of the present disclosure, a method for controlling an ultrasonic apparatus includes the steps of displaying sequentially a plurality of frame images generated based on ultrasonic signals, receiving a select instruction for selecting the frame image being displayed among the plurality of frame images, and displaying at least one of frame images, each of which has a motion blur factor equal to or less than a predetermined threshold value and is obtained prior to a select instruction input time, among the plurality of frame images when a motion blur factor of the frame image selected by the select instruction exceeds the threshold value or a substitute image display instruction is input.

Also, the method may further include the step of calculating a motion blur factor of an $N^{th}$ frame image based on a difference between the $N^{th}$ frame image (N is a natural number equal to or greater than 2) and an $N-1^{th}$ frame image, which is a previous frame image of the $N^{th}$ frame image, among the plurality of frame images.

Further, the displaying of at least one of the frame images, each of which has the motion blur factor equal to or less than the threshold value and is obtained prior to the select instruction input time, may display a frame image closest to the selected frame image among the frame images, each of which has the motion blur factor equal to or less than the threshold value and is obtained prior to the select instruction input time.

Furthermore, the displaying of at least one of the frame images, each of which has the motion blur factor equal to or less than the threshold value and is obtained prior to the select instruction input time, may display at least one frame image obtained during a time period in which a plurality of successive frame images, each of which has a motion blur factor equal to or less than the threshold value, are obtained prior to the select instruction input time, when the time period exceeds a predetermined threshold time.

Moreover, the displaying of at least one of the frame images, each of which has the motion blur factor equal to or less than the threshold value and is obtained prior to the select instruction input time, may display a frame image having a minimum motion blur factor among the plurality of successive frame images obtained during the time period.

Also, the displaying of at least one of the frame images, each of which has the motion blur factor equal to or less than the threshold value and is obtained prior to the select instruction input time, may include the steps of selecting multiple frame images being simultaneously displayed based on the motion blur factors among the plurality of successive frame images obtained during the time period, and displaying simultaneously the selected multiple frame images.

Further, the displaying of at least one of the frame images, each of which has the motion blur factor equal to or less than the threshold value and is obtained prior to the select instruction input time, may display the motion blur factors of the multiple frame images being simultaneously displayed in association with the multiple frame images.

Moreover, the method may further include the step of receiving a select instruction for selecting one among the multiple frame images being simultaneously displayed.

Also, the method may further include the step of magnifying and displaying a selected frame image when the select instruction is input to select one among the multiple frame images being simultaneously displayed.

Moreover, the method may further include the step of displaying information related to a motion blur factor of the selected frame image when the motion blur factor of the selected frame image exceeds the threshold value.

Also, the method may further include the step of outputting information related to a motion blur factor of the selected frame image as a sound when the motion blur factor of the selected frame image exceeds the threshold value.

Further, the displaying sequentially of the plurality of frame images generated based on the ultrasonic signals may include the steps of obtaining the ultrasonic signals containing information of a target object in real time, generating the plurality of frame images in real time based on the ultrasonic signals obtained in real time, and displaying sequentially the plurality of frame images generated in real time.

Furthermore, the method may further include the step of storing at least one among the plurality of frame images generated in real time.

Moreover, the storing of at least one among the plurality of frame images generated in real time may store frame images, each of which has a motion blur factor equal to or less than the threshold value, among the plurality of frame images generated in real time.

In accordance with one aspect of the ultrasonic apparatus and the method for controlling the same, a frame image having a small motion blur factor and obtained prior to a select instruction input time may be provided to the user as a substitute image so as to substitute a frame image having a large motion blur factor, which is selected by a select instruction from a user. As a result, accuracy of an ultrasonic diagnosis may be improved.

In accordance with another aspect of the ultrasonic apparatus and the method for controlling the same, a plurality of frame images, each of which has a motion blur factor smaller than that of a frame image selected by a select instruction from a user and having a large motion blur factor, may be provided to the user as candidate substitute images and an instruction for selecting one of the candidate substitute images to be substituted with the selected frame image may be received from the user. As a result, the user may directly select a frame image available for an ultrasonic diagnosis among the plurality of frame images.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION

Figure 1:
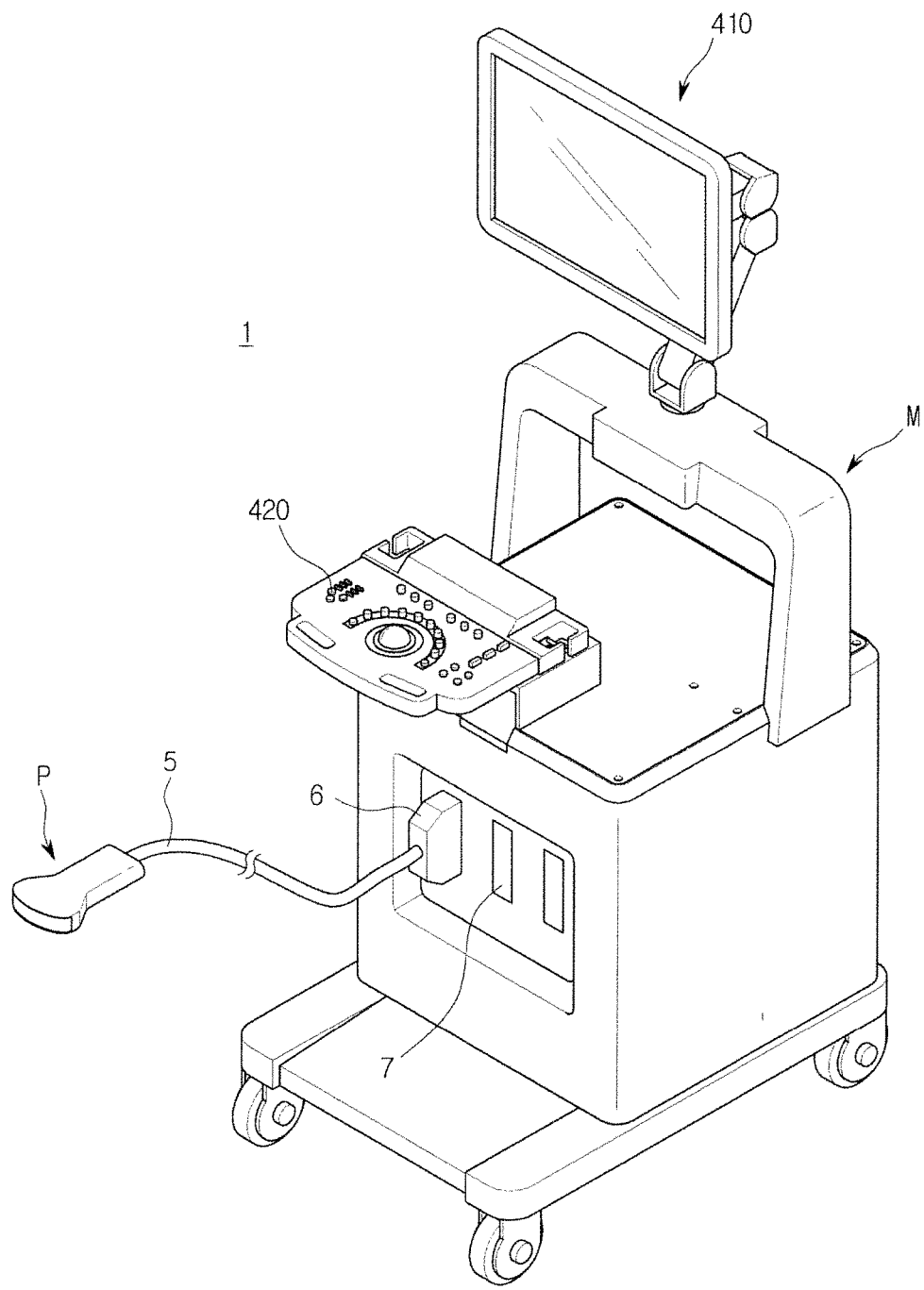
FIG. 1 is a perspective view of an ultrasonic apparatus according to one embodiment of the present invention.

Reference will now be made in detail to the embodiments of the present disclosure, examples of which are illustrated in the accompanying drawings, wherein like reference numerals refer to like elements throughout.

Hereinafter, embodiments of an ultrasonic apparatus and a method for controlling the same will be described in detail with reference to the accompanying drawings.

Figure 2:
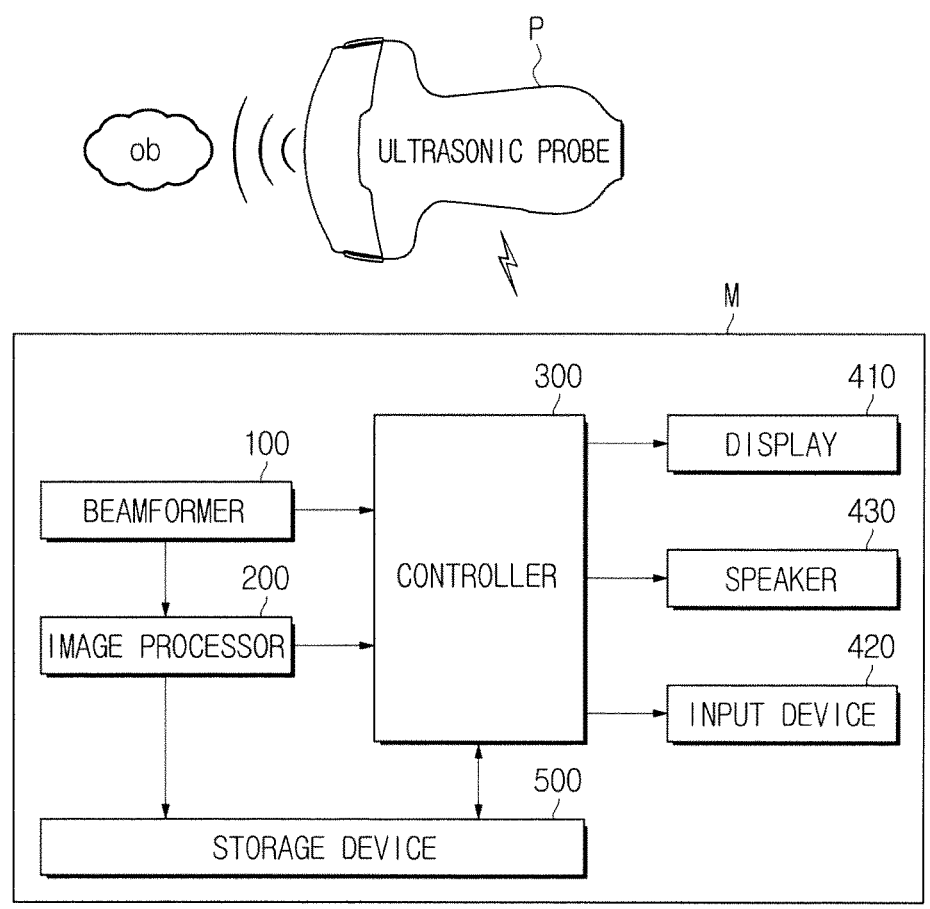
FIG. 2 is a control block diagram of the ultrasonic apparatus according to one embodiment of the present invention.

FIG. 1 is a perspective view of an ultrasonic apparatus according to one embodiment, and FIG. 2 is a control block diagram of the ultrasonic apparatus according to one embodiment.

As shown in FIG. 1, an ultrasonic apparatus 1 may include a main body M and an ultrasonic probe P.

The ultrasonic probe P may be a part contacting directly to a body surface of a target object to collect ultrasonic echoes containing information of the target object. For this purpose, the ultrasonic probe P may include a plurality of transducer elements capable of converting electrical signals into ultrasonic waves, and vice versa.

The plurality of transducer elements may be arranged on one surface of the ultrasonic probe P. The ultrasonic probe P at which the plurality of transducer elements are arranged one-dimensionally on one surface thereof is referred to as a 1-dimensional (1D) array probe. The 1D array probe includes a linear array probe at which transducer elements are arranged in a line, a phased array probe, and a convex array probe at which transducer elements are arranged in a curved shape.

Otherwise, the ultrasonic probe P at which transducer elements are two-dimensionally arranged is referred to as a 2-dimensional (2D) array probe. The transducer elements may be arranged on a plane surface of the 2D array probe. Alternatively, the transducer elements may be arranged in a curved shape on one surface of the 2D array probe.

The transducer elements may vibrate in response to transmitted signals provided from the main body M to generate ultrasonic waves. The ultrasonic waves generated as described above may be transmitted to an internal side of the target object. Also, the transducer elements may vibrate in response to ultrasonic echoes reflected from a predetermined portion of the internal side of the target object to generate received signals corresponding to the ultrasonic echoes. The received signals may be transmitted to the main body M to be used for generating an ultrasonic image.

Hereinafter, the transmitted signals received by the ultrasonic probe P and the received signals generated by the ultrasonic probe P are referred to as ultrasonic signals.

The ultrasonic probe P may generate ultrasonic signals at a predetermined time interval by collecting ultrasonic echoes in real time. The ultrasonic signals generated at the predetermined time interval may be a base of a frame image of an ultrasonic image.

The ultrasonic probe P may be provided to communicate with the main body M through a cable 5. For this purpose, the ultrasonic probe P may be connected to one end of the cable 5, and a male connector 6 may be connected to the other end thereof. The male connector 6 connected to the other end of the cable 5 may be physically connected to a female connector 7 of the main body M, such that the ultrasonic probe P may be connected to the main body M.

The ultrasonic probe P may transmit and receive ultrasonic signals to and from the main body M through the cable 5. Moreover, the ultrasonic probe P may receive a control signal from the main body M through the cable 5, thereby being controlled by the main body M.

In particular, when a control signal corresponding to a control instruction input through an input device 420 is generated in the main body M, the ultrasonic probe P may receive the control signal through the cable 5, thereby being controlled according to the control instruction. For example, when a control instruction for setting focal depths of ultrasonic signals to be transmitted, a size or a shape of an aperture of the ultrasonic probe P, a steering angle thereof, or the like is input through the input device 420, the main body M may generate a control signal corresponding to the control instruction. The control signal generated as described above may be transmitted to the ultrasonic probe P through the cable 5 to be used for performing a beamforming.

Unlike shown in FIG. 1, the ultrasonic probe P may be wirelessly connected to the main body M. In this case, the ultrasonic probe P may transmit and receive ultrasonic signals to and from the main body M according to a wireless communication method.

The ultrasonic probe P may be connected to the main body M by adopting one of wireless communication methods well-known in the related art. For example, the ultrasonic probe P may be connected to the main body M through wireless Internet methods including a wireless local area network (WLAN), a wireless fidelity (Wi-Fi), a wireless broadband (Wibro), a world interoperability for microwave access (Wimax), a high speed downlink packet access (HSDPA), and the like, or near field communication methods including a Bluetooth, a radio frequency identification (RFID), an infrared data association (IrDA), an ultra wideband (UWB), a Zigbee, and the like.

As shown in FIG. 2, the main body M may include a beamformer 100, an image processor 200, a controller 300, a storage device 500, the input device 420, a display 410, and a speaker 430.

The speaker 430 may inform a user of information related to a status of the ultrasonic apparatus 1 by outputting a predetermined sound. For example, the speaker 430 may output information related to a power supply, an image display, and the ultrasonic probe P of the ultrasonic apparatus 1 as a sound.

Also, the speaker 430 may inform the user of a motion blur occurrence in a frame image being currently selected by the user by outputting a sound, and if a frame image substituted for the motion blurred frame image currently selected is being displayed, the speaker 430 may inform the user of displaying the substituted frame image. A detailed explanation of the aforementioned description will be followed.

The controller 300 may control an overall operation of the ultrasonic apparatus 1. In particular, the controller 300 may control not only operations of the beamformer 100 and the image processor 200 which are provided inside the main body M, but also operations of the ultrasonic probe P connected to the main body M by wires or wirelessly, the input device 420, and/or the display 410.

For example, the controller 300 may compute delay profiles with respect to the plurality of transducer elements to calculate time delays on the basis of the delay profiles. Using the calculated time delays, the controller 300 may control the beamformer 100 to perform a beamforming on ultrasonic signals. Also, the controller 300 may generate a control signal with respect to each of components of the ultrasonic apparatus 1 according to a control instruction of the user input through the input device 420 to control the ultrasonic apparatus 1.

The beamformer 100 may perform a beamforming on ultrasonic signals so as to enable the ultrasonic probe P to transmit ultrasonic waves, or on ultrasonic signals received from the ultrasonic probe P. At this point, the beamforming may mean a method for aligning ultrasonic waves transmitted to a predetermined point of a target object OB, or aligning ultrasonic echoes reflected from the predetermined point thereof by delaying the ultrasonic waves or the ultrasonic echoes. This is for correcting differences between arrival times of the ultrasonic echoes reaching the predetermined point of the target object OB or being reflected from the predetermined point thereof, at the plurality of transducer elements.

The beamformer 100 may adopt one of beamforming methods well-known in the related art, a combination thereof, or a selective combination thereof.

The ultrasonic signals undergone the beamforming in the beamformer 100 may be transmitted to the image processor 200, which will be described later, to be used for generating an ultrasonic image.

The image processor 200 may process the ultrasonic signals undergone the beamforming in the beamformer 100 to generate and transmit an ultrasonic image of the target object OB to the display 410, thereby visually providing the user with anatomical information of the target object OB. For this purpose, the image processor 200 may be implemented in the form of hardware including a microprocessor, and, alternatively, may be implemented by software to be operated on hardware.

As described in detail, when the ultrasonic probe P collects ultrasonic echoes in real time to generate ultrasonic signals at a predetermined time interval, the image processor 200 may generate frame images at a predetermined time interval on the basis of the generated ultrasonic signals.

The storage device 500 may store the ultrasonic image generated by the image processor 200. If the image processor 200 generates a plurality of frame images as the ultrasonic image, the storage device 500 may sequentially or selectively store therein the plurality of frame images.

Furthermore, the storage device 500 may store in advance various information used for controlling the ultrasonic apparatus 1. For example, the storage device 500 may store in advance information related to a power supply control of the ultrasonic apparatus 1, and information used for a transmit beamforming and/or a receive beamforming.

Also, the storage device 500 may store in advance a filter and an algorithm used for determining motion blur factors of the frame images, and a threshold value and a threshold time of a motion blur factor, which are criteria for determining whether or not a substitute frame image is needed to be displayed.

For this purpose, the storage device 500 may be implemented by at least one type storage medium among memories including a flash memory type, a hard disk type, a multimedia card micro type, a card type (for example, a secure digital (SD) memory card, an extreme digital (XD) memory card, or the like), a random access memory (RAM), a static random access memory (SRAM), a read-only memory (ROM), an electrically erasable programmable read-only memory (EEPROM), a programmable read-only memory (PROM), a magnetoresistive random access memory, a magnetic disk, and an optical disk.

The display 410 may be connected to the main body M to display the ultrasonic image generated in the main body M. At this point, the ultrasonic image displayed by the display 410 may be a still image at a predetermined time, or a moving image consisting of a plurality of frame images.

Moreover, the display 410 may display applications related to operations of the ultrasonic apparatus 1. For example, the display 410 may display menus and guide items necessary for an ultrasonic diagnosis.

The display 410 may be implemented by a cathode ray tube (CRT), a liquid crystal display (LCD), an electroluminescence display (ELD), a field emission display (FED), a plasma display, a thin film transistor LCD (TFT-LCD), or an organic light emitting diode (OLED), but it is not limited thereto.

Also, the display 410 may be designed not only to display the ultrasonic image in two dimension but also to provide the user with a three dimensional image. In particular, the display 410 may designed to allow the user to differently recognize an image through a left eye and a right eye, thereby providing the user with the three dimensional image due to binocular parallax.

Although the ultrasonic apparatus 1 equipped with one display 410 is illustratively shown in FIG. 1, a plurality of displays 410 may be provided. At this point, each of the plurality of displays 410 may display a different image, and at least two thereof may display the same image.

The input device 420 is provided to be connected to the main body M to receive instructions related to operations of the ultrasonic apparatus 1. For example, the input device 420 may receive an ultrasonic diagnosis start instruction, or a mode select instruction of the ultrasonic image.

An example in which the input device 420 is connected by wire to the main body M is illustratively shown in FIG. 1, but the input device 420 may be implemented to transmit to the main body M a control instruction received through a wireless communication method.

The input device 420 may include a variety of means including a keyboard, a mouse, a trackball, a tablet, a touch screen module, or the like, which enables the user to input a control instruction.

Meanwhile, as described in detail, the display 410 may sequentially display the plurality of frame images thereon. At this point, the user may freeze the sequential receiving of the plurality of frame images, and continuously receive one frame image thereof.

For this purpose, the input device 420 may receive a select instruction for selecting one frame image being currently displayed. If the select instruction is input from the user, the controller 300 may control the display 410 to freeze the sequential displaying of the plurality of frame images, thereby continuously providing the user with a frame image being displayed at a current time, that is, at an input time of the select instruction.

Figure 3:
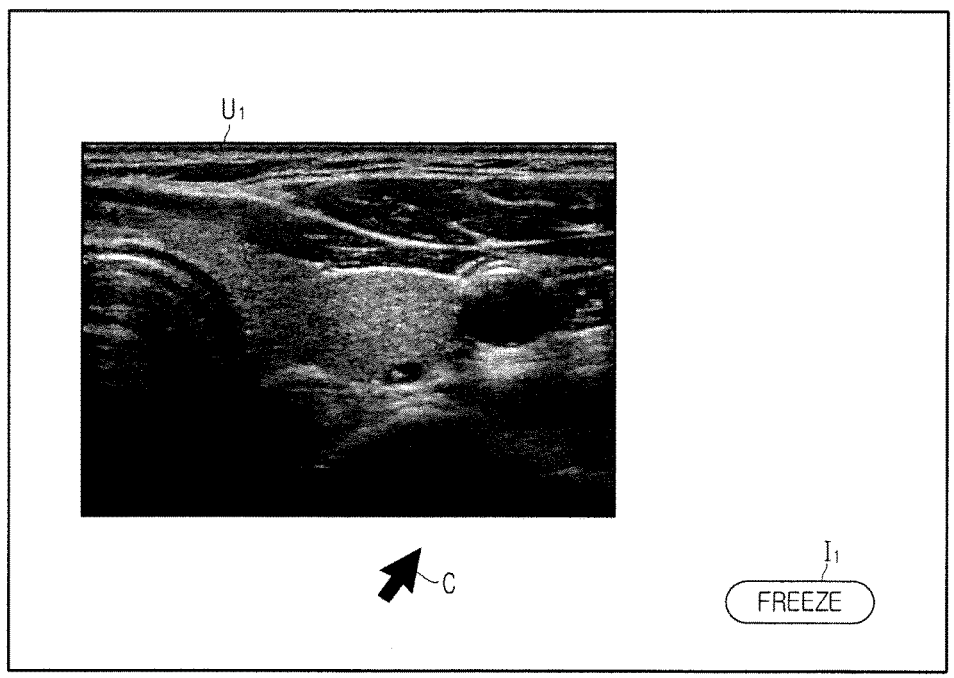
FIG. 3 is a view illustrating one embodiment of a method for displaying an image freeze icon on a display according to one embodiment of the present invention.
Figure 4:
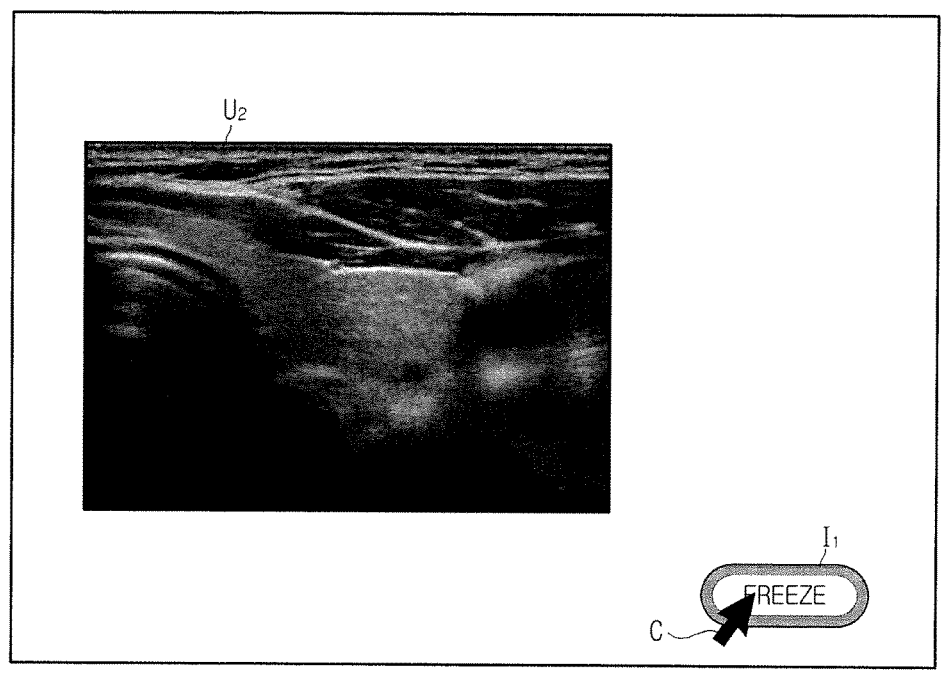
FIG. 4 is a view illustrating an example of a motion blur occurrence on a frame image displayed on the display when a select instruction is input according to one embodiment of the present invention.

FIG. 3 is a view illustrating one embodiment of a method for displaying an image freeze icon on the display 410 according to one embodiment, and FIG. 4 is a view illustrating a motion blur occurrence in a frame image being displayed on the display 410 when the select instruction is input according to one embodiment.

As described in detail, the display 410 may sequentially display the plurality of frame images. While visually verifying the plurality of frame images being sequentially displayed, the user may acquire anatomical information of an internal side of the target object OB.

The plurality of frame images displayed as described above may be generated in real time from ultrasonic signals acquired by the ultrasonic probe P in real time, or may be sequentially displayed through the display 410 after being stored in the storage device 500 in advance.

Also, the display 410 may display a freeze icon in association with the frame image. The user may click the freeze icon through the input device 420, and clicking the freeze icon may mean an input of a select instruction for a frame image being displayed at a clicking time.

Consequently, the display 410 may freeze the sequential displaying of the plurality of frame images to continuously display the frame image being displayed at the clicking time. Therefore, the user may precisely verify a frame image being displayed at a desired time.

Typically, while holding the ultrasonic probe P in one hand, the user may move a position of the ultrasonic probe P to receive in real time anatomical images of target objects OB different from each other. Therefore, the user may visually verify viscera or lesions of the internal side of the target object OB to perform an ultrasonic diagnosis on the target object OB.

At this point, when the frame image being displayed on the display 410 contains viscera or lesions to be observed, the user may fix a position of the ultrasonic probe P and then may use the other hand to input through the input device 420 a select instruction for a frame image being currently displayed, that is, may click the freeze icon. Consequently, the display 410 continuously displays the selected frame image, such that the user may perform a precise diagnosis on the viscera or lesions to be observed.

However, there may be a problem in which a time difference between a time when the user visually verifies a desired frame image and a time when the user inputs the select instruction through the input device 420 occurs.

The user may visually verify a frame image $U_1$ shown in FIG. 3 to input a select instruction for the frame image $U_1$. With reference to FIG. 4, the user may input the select instruction by clicking the freeze icon displayed on the display 410 using a cursor C. At this point, the user may operate the ultrasonic probe P and the input device 420 using different hands, such that a position of the ultrasonic probe P may be moved when the user manipulates the input device 420. As a result, unlike the user's intent, a frame image $U_2$ may be selected.

It may not be a problem in case that the frame images $U_1$ and $U_2$ definitely show viscera or lesions to be observed by the user. However, as shown in FIG. 4, when motion blurs occur in the frame image $U_2$, it may be difficult for the user to verify shapes of the lesions or the viscera of the internal side of the target object OB through the frame image $U_2$.

In order to address such a problem, the ultrasonic apparatus 1 according to one embodiment of the disclosed invention may display a substitute image instead of the selected frame image when a motion blurred frame image is selected rather than the frame image to which the user really wants to observe.

Referring back to FIG. 2, the controller 300 may receive the plurality of frame images, which are generated in the image processor 200 in real time, or stored in the storage device 500 in advance, to digitize motion blur of each of the plurality of frame images, thereby obtaining a motion blur factor.

The controller 300 may use a previous frame image, that is, an N−1$^{th}$ frame image (N is a natural number equal to or greater than 2) so as to obtain a motion blur factor of an N$^{th}$ frame image. Using the N−1$^{th}$ frame image, the controller 300 may obtain an edge image of the N$^{th}$ frame image and then apply an edge filter to the obtained edge image to obtain a motion blur factor.

In particular, the controller 300 may obtain the edge image of the N$^{th}$ frame image having pixel values consisting of pixel value differences between the N$^{th}$ frame image and the N−1$^{th}$ frame image. Thereafter, the controller 300 may apply a 3×3 edge filter to each pixel of the edge image. The controller 300 may separately obtain an X-axis pixel value and a Y-axis pixel value of each pixel by applying an edge filter to each pixel of the edge image.

At this point, the controller 300 may adopt at least one edge filter well-known in the related art among, for example, a Roberts mask, a Prewitt mask, a Soble mask, a Chen-Frei mask, and the like as the 3×3 edge filter.

After obtaining the X-axis pixel value and the Y-axis pixel value of each pixel, the controller 300 may use the X- and Y-axis pixel values to obtain a filtered edge image of the N$^{th}$ frame image. In particular, the controller 300 may obtain each pixel value of the filtered edge image according to Equation 1.

$$G^N(j,k) = \sqrt{G_x(j,k)^2 + G_y(j,k)^2} \qquad \text{[Equation 1]}$$

Herein, $G^N(j,k)$ may represent a pixel value at a j$^{th}$ column and a k$^{th}$ row of the filtered edge image of the N$^{th}$ frame image, $G_x(j,k)$ may represent an X-axis pixel value at the j$^{th}$ column and the k$^{th}$ row of the filtered edge image of the N$^{th}$ frame image, and $G_y(j,k)$ may represent a Y-axis pixel value at the j$^{th}$ column and the k$^{th}$ row of the filtered edge image of the N$^{th}$ frame image.

Finally, the controller 300 may obtain a motion blur factor of the N$^{th}$ frame image using these pixel values. In particular, the motion blur factor F of the N$^{th}$ frame image may be calculated according to Equation 2.

$$F^N = \sum_{j,k} \{G^{N-1}(j,k) - G^N(j,k)\} \qquad \text{[Equation 2]}$$

Herein, $F^N$ may represent the motion blur factor of the N$^{th}$ frame image, $G^{N-1}(j,k)$ may represent a pixel value at the j$^{th}$ column and the k$^{th}$ row of the filtered edge image of the N−1$^{th}$ frame image, and $G^N(j,k)$ may represent the pixel value at the j$^{th}$ column and the k$^{th}$ row of the filtered edge image of the N$^{th}$ frame image.

Using the process described in detail, the controller 300 may obtain a motion blur factor of each of the plurality of frame images through the digitization process.

Also, if a motion blur factor of a frame image selected by the user exceeds a threshold value, the controller 300 may display at least one of frame images, each of which has a motion blur factor equal to or less than the threshold value and is obtained prior to a select instruction input time, among the plurality of frame images.

At this point, the threshold value of the motion blur factor Fay be determined by a calculation in the ultrasonic apparatus 1, or may be directly input by the user through the input device 420.

Figure 5:
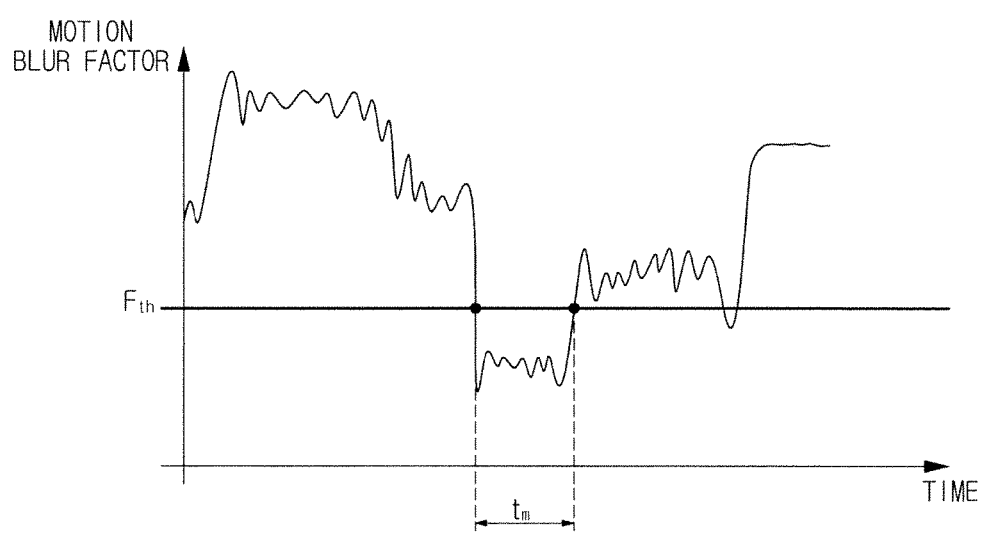
FIG. 5 is a graph of motion blur factors for times prior to a select instruction input time according to one embodiment of the present invention.

FIG. 5 is a graph of motion blur factors for times prior to a select instruction input time according to one embodiment.

According to the process described in detail, the controller 300 may obtain in advance motion blur factors of a currently displayed frame image and a previously displayed frame image. And, if a select instruction for the currently displayed frame image is input from the user, the controller 300 may determine whether or not the motion blur factor of the currently displayed frame image at a select instruction input time exceeds a threshold value.

The threshold value may mean a maximum motion blur factor enabling an ultrasonic diagnosis, such that the controller 300 may continuously display the selected image through the display 410 if a motion blur factor of the selected image is equal to or less than the threshold value.

On the contrary, if the motion blur factor of the selected image exceeds the threshold value, the controller 300 may select a frame image to be substituted for the selected image using the motion blur factors of the plurality of frame images obtained prior to the select instruction input time.

With reference to FIG. 5, the controller 300 may verify a time period $t_m$ during which the motion blur factors of multiple frame images obtained prior to the select instruction input time among the plurality of frame images are equal to or less than a threshold value $F_{th}$. If the verified time period $t_m$ exceeds a predetermined threshold time $t_{th}$, the controller 300 may select at least one of the multiple frame images obtained during the time period $t_m$ among the plurality of frame images as a substitute image for the selected frame image.

The controller 300 according to one embodiment may select a frame image having a minimum motion blur factor among the multiple frame images obtained during the time period $t_m$ as a substitute image. The display 410 may display the selected frame image thereon to provide an ultrasonic image meeting the user's selection intent.

Figure 6A:
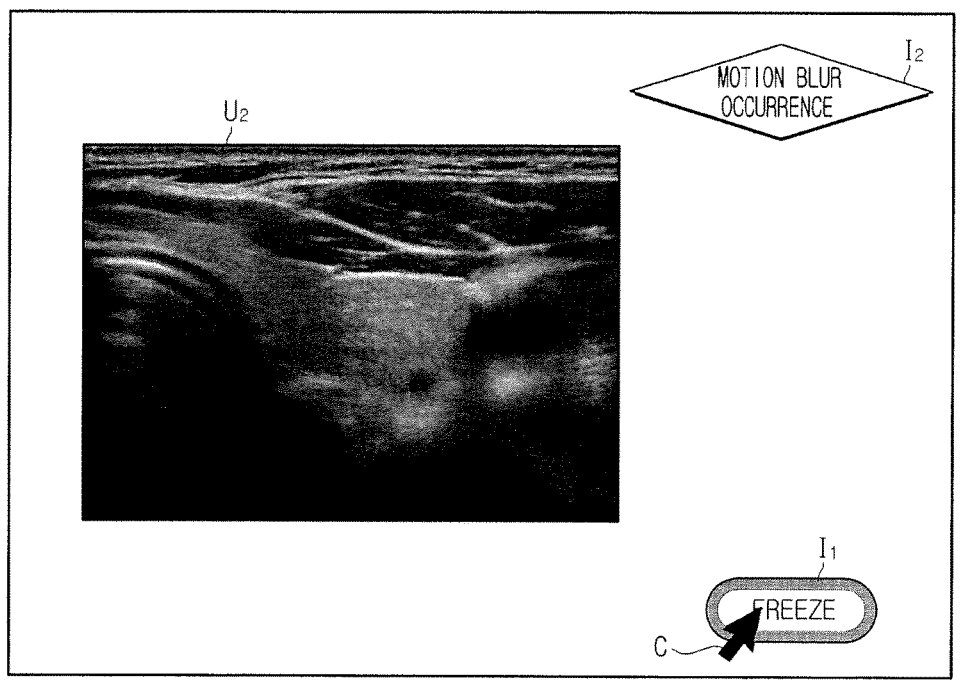
FIGS. 6A and 6B are views for describing a method for displaying a substitute image on the display according to one embodiment of the present invention.
Figure 6B:
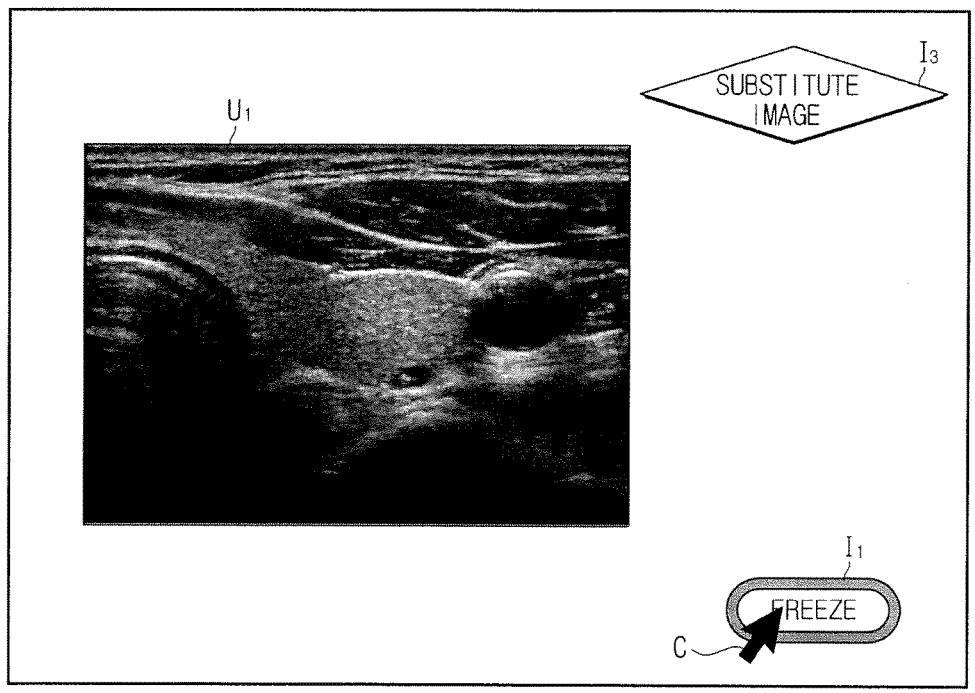

FIGS. 6A and 6B are views for describing a method for displaying a substitute image on the display 410 according to one embodiment.

As described in detail, the user may input the select instruction by clicking the freeze icon displayed on the display 410. FIG. 6A illustratively shows an example in which the frame image $U_2$ being displayed at a time when the select instruction is input is selected although the user wants to select a non-motion blurred frame image.

The controller 300 may verify a motion blur factor of the frame image U2 and then control the display 410 to display thereon an informative icon $I_2$ for informing about a motion blur occurrence when the verified motion blur factor exceeds a threshold value.

Alternatively, unlike shown in FIG. 6A, the controller 300 may verify the motion blur factor of the frame image $U_2$ and then control the speaker 430 to output a sound for informing about a motion blur occurrence when the verified motion blur factor exceeds the threshold value.

After informing the user of the motion blur occurrence, the controller 300 may verify whether or not a time period obtaining frame images, each of which has a motion blur factor equal to or less than a threshold value, prior to the select instruction input time exceeds a threshold time. If the time period obtaining the frame images, each of which has a motion blur factor equal to or less than the threshold value, exceeds the threshold time, the controller 300 may select a frame image having a minimum motion blur factor among the frame images obtained during the time period.

With reference to FIG. 6B, the controller 300 may control the display 410 to display thereon the frame image $U_1$ having the minimum motion blur factor during the time period. Therefore, a substitute image closest to a non-motion blurred frame image which the user wants to select may be provided to the user.

Moreover, the controller 300 may control the display 410 to display thereon a substitute image display informing icon $I_3$ for informing about a displaying of the substitute image instead of the selected image. Alternatively, the controller 300 may control the speaker 430 to output a sound for informing about the displaying of the substitute image instead of the selected image.

The controller 300 according to another embodiment may simultaneously display a predetermined number of frame images among a plurality of frame images obtained during the time period $t_m$ as candidate substitute images.

Figure 7:
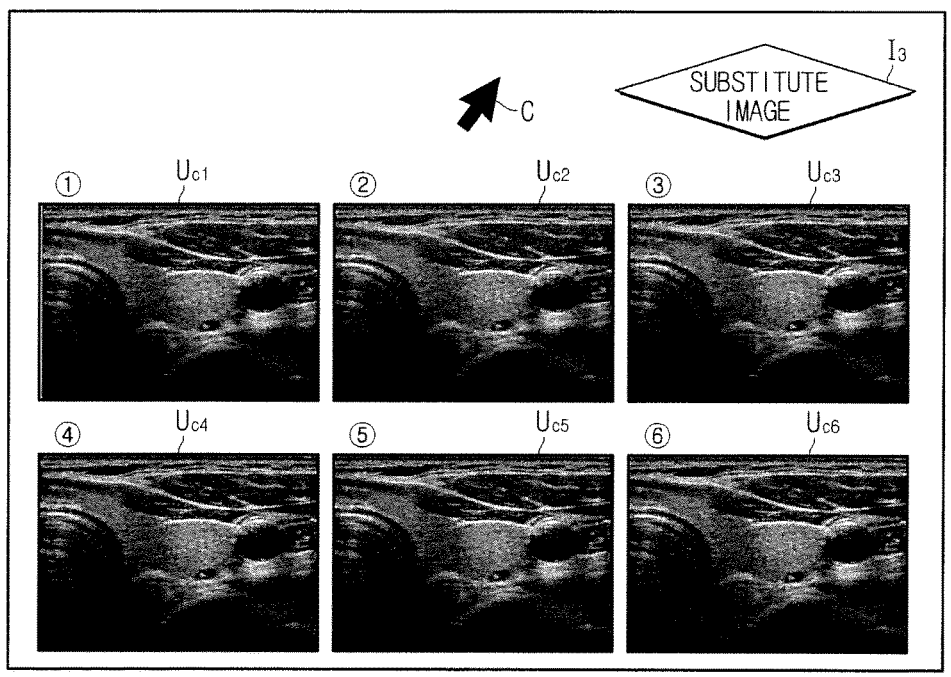
FIG. 7 is a view for describing a method for displaying candidate substitute images on the display according to one embodiment of the present invention.
Figure 8A:
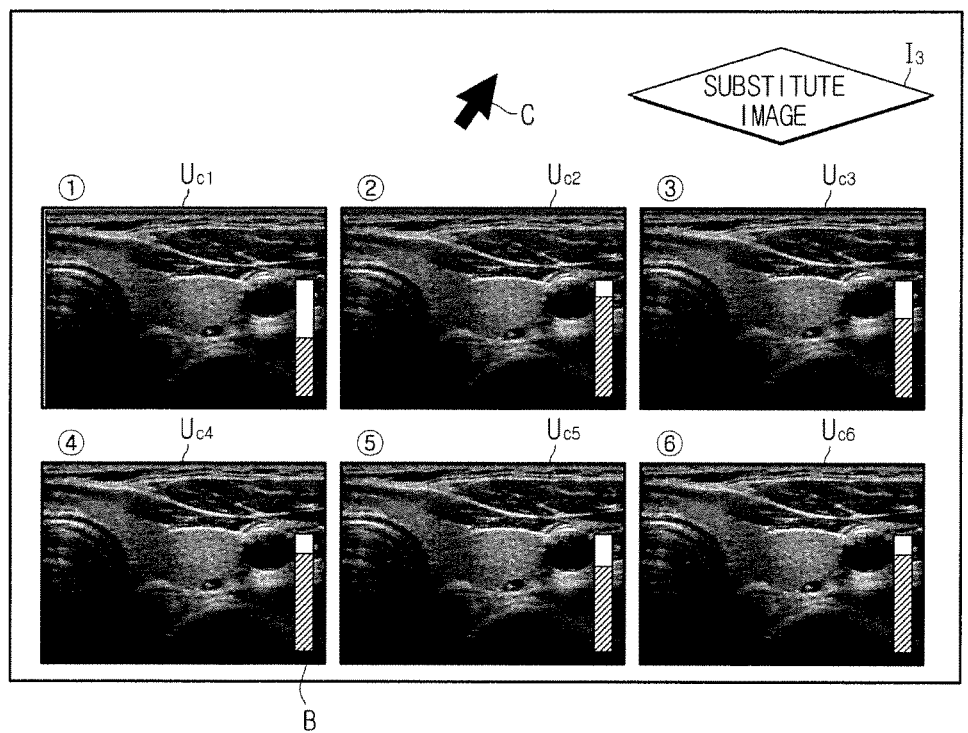
FIGS. 8A and 8B are views for describing a method for displaying motion blur factors of the candidate substitute images on the display according to one embodiment of the present invention.
Figure 8B:
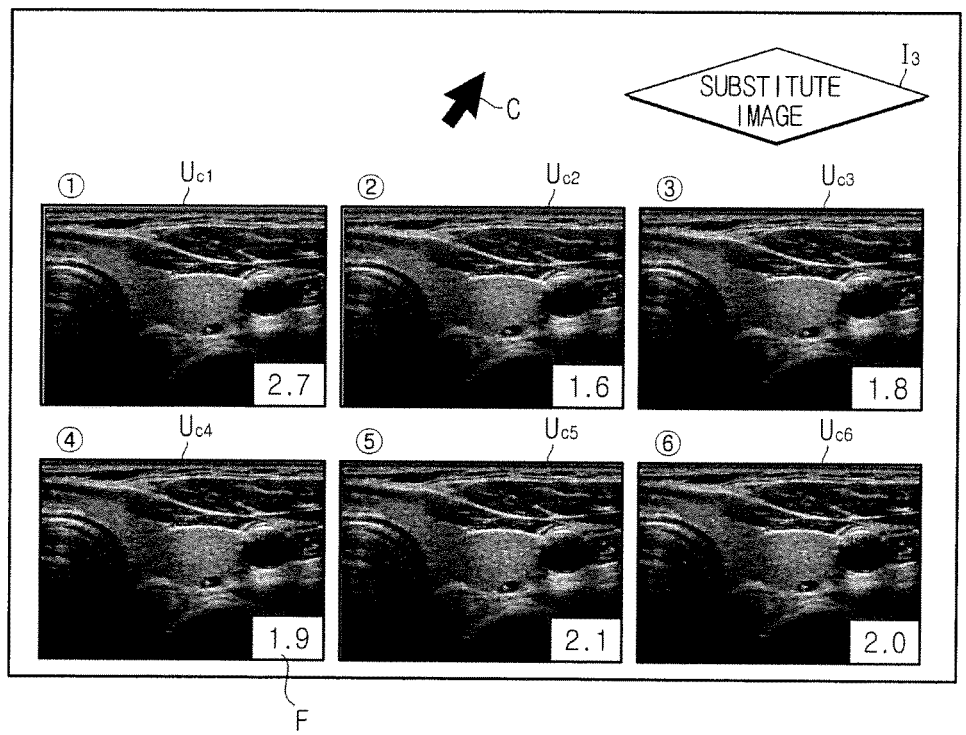
Figure 9:
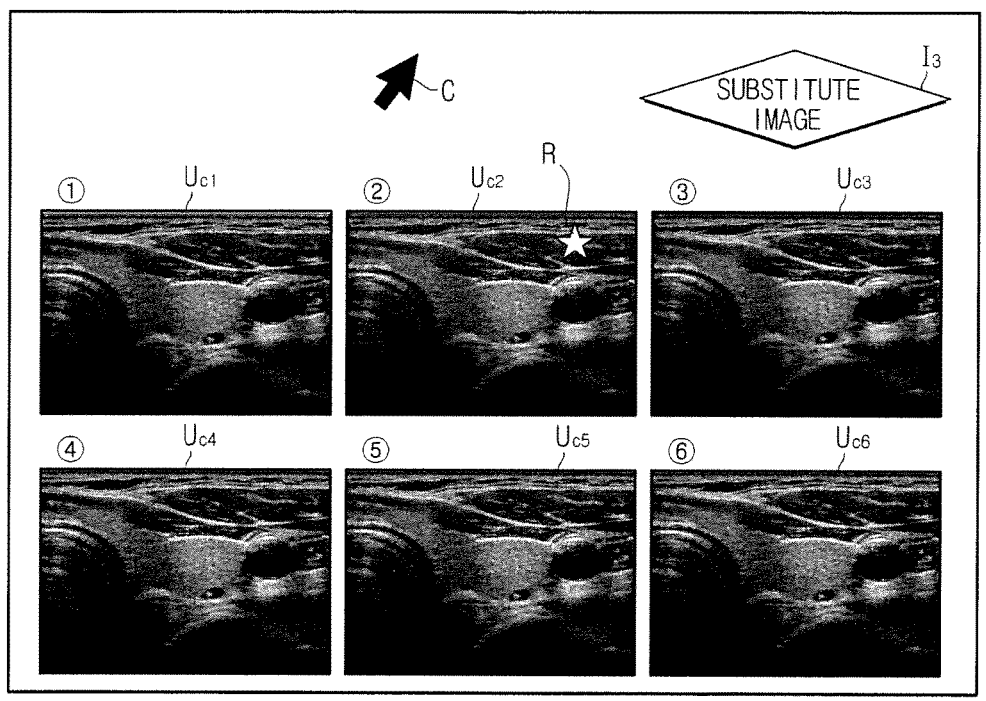
FIG. 9 is a view for describing a method for displaying recommended substitute images on the display according to one embodiment of the present invention.

FIG. 7 is a view for describing a method for displaying candidate substitute images on the display 410 according to one embodiment, FIGS. 8A and 8B are views for describing a method for displaying motion blur factors of the candidate substitute images on the display 410 according to one embodiment, and FIG. 9 is a view for describing a method for displaying recommended substitute images on the display 410 according to one embodiment.

When a motion blur occurs in the selected image, the controller 300 may control the display 410 to display simultaneously thereon a predetermined number of frame images among the plurality of frame images obtained prior to the select instruction input time as candidate substitute images.

In particular, the controller 300 may verify whether or not a time period obtaining frame images, each of which has a motion blur factor equal to or less than a threshold value, prior to the select instruction input time exceeds a threshold time.

If the time period obtaining the frame images having the motion blur factors equal to or less than the threshold value exceeds the threshold time, the controller 300 may select a predetermined number of frame images obtained during the time period in an ascending order of the motion blur factors thereof as candidate substitute images.

As shown in FIG. 7, the controller 300 may select six frame images obtained during the time period in the ascending order of the motion blur factors thereof as candidate substitute images $U_{c1}$ to $U_{c6}$.

The input device 420 may receive from the user a select instruction for selecting one of a plurality of candidate substitute images as a substitute image. For example, the user may move the cursor C through the input device 420 and then click one of the plurality of candidate substitute images to input the select instruction for selecting a substitute image.

Therefore, the user may directly select a substitute image useful and available for the ultrasonic diagnosis.

Alternatively, the controller 300 may control the display 410 to display thereon a motion blur factor corresponding to each of the plurality of candidate substitute images in association therewith. FIG. 8A shows illustratively an example in which the display 410 displays in a bar shape B the motion blur factor corresponding to each of the plurality of candidate substitute images in association therewith, and FIG. 8B shows illustratively an example in which the display 410 displays as a digit F the motion blur factor corresponding to each of the plurality of candidate substitute images in association therewith.

Therefore, the user may easily select a substitute image having a small motion blur factor by visually verifying the motion blur factor of each of the plurality of frame images displayed in association therewith on a screen.

Alternatively, the controller 300 may recommend a candidate substitute image having a minimum motion blur factor among the plurality of candidate substitute images as a substitute image. With reference to FIG. 9, the display 410 may display a mark R for recommending the user to select a candidate substitute image $U_{C2}$ thereon as a substitute image.

As such, the user may be aided in selecting a substitute image having a small motion blur factor.

Heretofore, it has been illustratively described for an example in which the ultrasonic apparatus 1 adaptively displays at least one among frame images having motion blur factors equal to or less than a threshold value and obtained prior to a select instruction input time when a motion blur factor of a frame image selected by the user exceeds the threshold value. Alternatively, when a substitute image display instruction is input from the user after a frame image selected by the user is displayed, the ultrasonic apparatus 1 may possibly display at least one among frame images having motion blur factors equal to or less than the threshold value and obtained prior to the select instruction input time.

Figure 10:
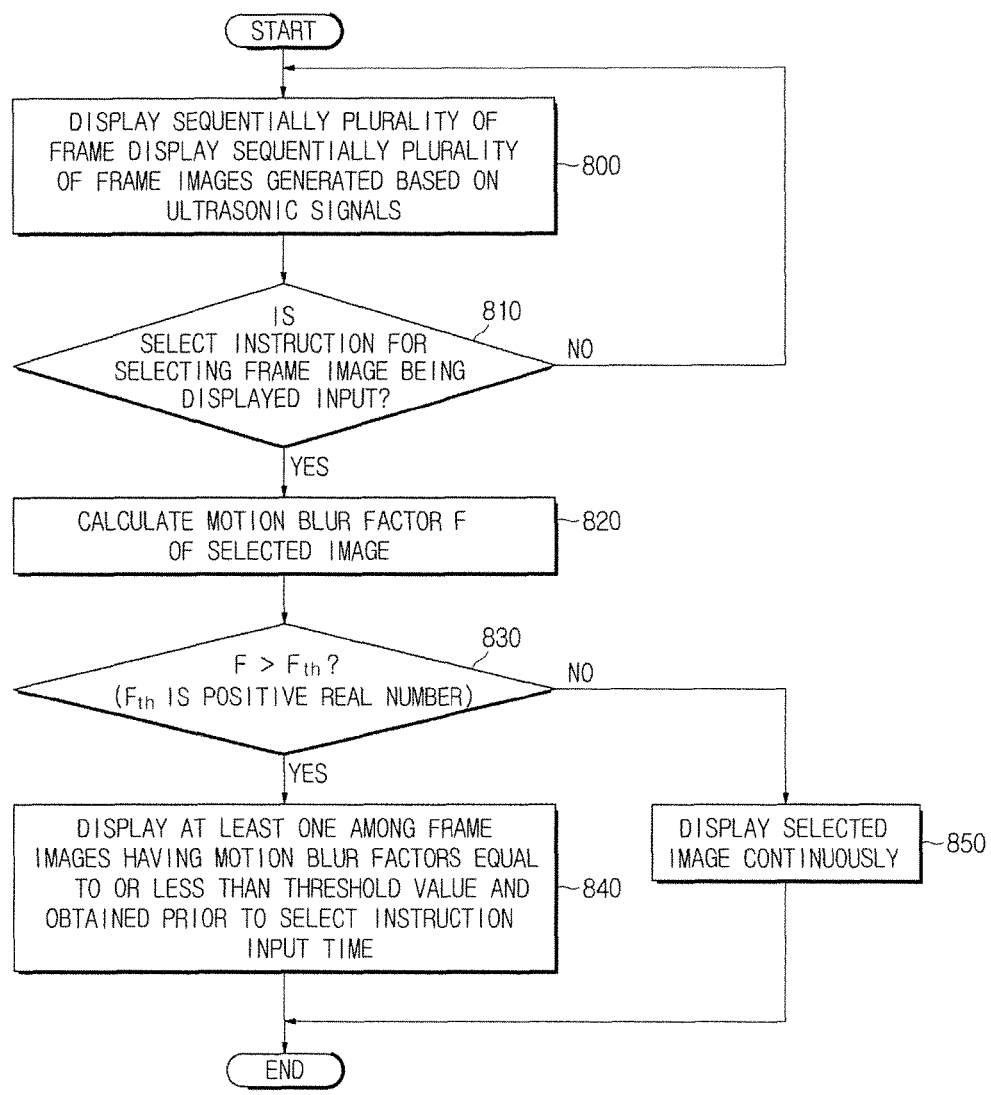
FIG. 10 is a flowchart of a method for controlling the ultrasonic apparatus according to one embodiment of the present invention.

FIG. 10 is a flowchart of a method for controlling the ultrasonic apparatus 1 according to one embodiment.

Firstly, the ultrasonic apparatus 1 may sequentially display a plurality of frame images generated based on ultrasonic signals (800). At this point, the ultrasonic apparatus 1 may convert the ultrasonic signals acquired in real time through the ultrasonic probe P into a plurality of frame images in real time, thereby sequentially displaying the plurality of frame images. Alternatively, the ultrasonic apparatus 1 may store in advance the plurality of frame images and then display sequentially the plurality of stored frame images.

Thereafter, the ultrasonic apparatus 1 may verify whether or not a select instruction for selecting a frame image being displayed is input in Operation 810. If the select instruction for selecting the frame image being displayed is not input, the ultrasonic apparatus 1 may continue to display the plurality of frame images, sequentially.

Otherwise, if the select instruction for selecting the frame image being displayed is input, the ultrasonic apparatus 1 may calculate a motion blur factor F of the selected image in Operation 820. Herein, the motion blur factor F may be calculated by obtaining an edge image of the selected frame image using a difference between the selected frame image and a previous frame image to apply an edge filter to the obtained edge image.

After calculating the motion blur factor F, the ultrasonic apparatus 1 may verify whether or not the motion blur factor F exceeds a predetermined threshold value $F_{th}$ in Operation 830. Herein, the threshold value $F_{th}$ may mean a maximum motion blur factor not requiring a substitute image.

At this point, the threshold value $F_{th}$ may be determined through a calculation in the ultrasonic apparatus 1, or otherwise the user may directly input the threshold value $F_{th}$.

If the motion blur factor F of the selected frame image exceeds the threshold value $F_{th}$, the ultrasonic apparatus 1 may display at least one among a plurality of frame images having motion blur factors equal to or less than the threshold value $F_{th}$ and obtained prior to the select instruction input time as a substitute image in Operation 840. As a result, a non-motion blurred image may be provided to the user, such that the user may perform a more precise ultrasonic diagnosis.

On the contrary, if the motion blur factor F of the selected frame image is equal to or less than the threshold value $F_{th}$, the ultrasonic apparatus 1 may continuously display the selected image in Operation 850. This is because the selected image has the motion blur factor F not requiring a substitute image.

Although a few embodiments of the present disclosure have been shown and described, it would be appreciated by those skilled in the art that changes may be made in these embodiments without departing from the principles and spirit of the invention, the scope of which is defined in the claims and their equivalents.

What is claimed is:

1. An ultrasonic apparatus comprising:
an image processor configured to generate a plurality of frame images based on ultrasonic signals;
a display configured to display the plurality of frame images, sequentially;
an input device configured to receive a select instruction, for selecting a frame image being displayed on the display among the plurality of frame images; and
a controller configured to control the display to display at least one of the plurality of frame images, each of which has a motion blur factor equal to or less than a predetermined threshold value and is obtained prior to a select instruction input time, among the plurality of frame images when a motion blur factor of the frame image selected by the select instruction exceeds the threshold value or a substitute image display instruction is input,
wherein the at least one of the plurality of frame images to be displayed is a frame image that has been obtained at a point of time closest to the select instruction input time among the plurality of frame images, each of which has the motion blur factor equal to or less than the threshold value and is obtained prior to the select instruction input time.

2. The ultrasonic apparatus of claim 1, wherein the controller calculates a motion blur factor of an $N^{th}$ frame image based on a difference between the $N^{th}$ frame image (N is a natural number equal to or greater than 2) and an $N-1^{'''}$ frame image, which is a previous frame image of the $N^{th}$ frame image, among the plurality of frame images.

3. The ultrasonic apparatus of claim 1, wherein the controller controls the display to display at least one frame image obtained during a time period in which a plurality of successive frame images, each of which has a motion blur factor equal to or less than the threshold value, are obtained prior to the select instruction input time, when the time period exceeds a predetermined threshold time.

4. The ultrasonic apparatus of claim 3, wherein the controller controls the display to display a frame image having a minimum motion blur factor among the plurality of successive frame images obtained during the time period.

5. The ultrasonic apparatus of claim 3, wherein the controller controls the display to display simultaneously multiple frame images selected based on the motion blur factors among the plurality of successive frame images obtained during the time period.

6. The ultrasonic apparatus of claim 5, wherein the display displays the motion blur factors of the multiple frame images being simultaneously displayed in association with the multiple frame images.

7. The ultrasonic apparatus of claim 5, wherein the input device receives a select instruction for selecting one among the multiple frame images being simultaneously displayed, and wherein the controller controls the display to magnify and display a selected frame image when the select instruction is input to select one among the multiple frame, images being simultaneously displayed.

8. The ultrasonic apparatus of claim 1, wherein the controller controls the display to display information related to a motion blur factor of the selected frame image when the motion blur factor of the selected frame image exceeds the threshold value.

9. The ultrasonic apparatus of claim 1, further comprising:
an ultrasonic probe configured to obtain the ultrasonic signals containing information of a target object in real time,
wherein the image processor generates the plurality of frame images in real time based on the ultrasonic signals obtained in real time; and
further comprising:
a storage device configured to store at least one among the plurality of frame images generated in real time,
wherein the controller controls the storage device to store frame images, each of which has a motion blur factor equal to or less than the threshold value, among the plurality of frame images generated in real time.

10. A method for controlling an ultrasonic apparatus, comprising, the steps of:
displaying sequentially a plurality of frame images generated based on ultrasonic signals;
receiving a select instruction for selecting a frame image being displayed among the plurality of frame images; and
displaying at least one of the plurality of frame images, each of which has a motion blur factor equal to or less than a predetermined threshold value and is obtained prior to a select instruction input time, among the plurality of frame images when a motion blur factor of the frame image selected by the select instruction exceeds the threshold value or a substitute image display instruction is input,
wherein in the displaying of the at least one of the plurality of frame images, the at least one of the plurality of frame images to be displayed is a frame image that has been obtained at a point of time closest to the select instruction input time among the plurality of frame images, each of which has the motion blur factor equal to or less than the threshold value and is obtained prior to the select instruction input time.

11. The method of claim 10, further comprising the step of:
calculating a motion blur factor of an Nth frame image based on a difference between the Nth frame image (N is a natural number equal to or greater than 2) and an N−1th frame image, which is a previous frame image of the Nth frame image, among the plurality of frame images.

12. The method of claim 10, wherein the displaying of the at least one of the plurality of frame images, each of which has the motion blur factor equal to or less than the threshold value and is obtained prior to the select instruction input time, displays at least one frame image obtained during a time period in which a plurality of successive frame images, each of which has a motion blur factor equal to or less than the threshold value, are obtained prior to the select instruction input time, when the time period exceeds a predetermined threshold time.

13. The method of claim 12, wherein the displaying of the at least one of the plurality of frame images, each of which has the motion blur factor equal to or less than the threshold value and is obtained prior to the select instruction input time, displays a frame image having a minimum motion blur factor among the plurality of successive frame images obtained during the time period.

14. The method of claim 12, wherein the displaying of the at least one of the plurality of frame images, each of which has the motion blur factor equal to or less than the threshold value and is obtained prior to the select instruction input time, includes the steps of:
selecting multiple frame images being simultaneously displayed based on the motion blur factors among the plurality of successive frame images obtained during the time period; and
displaying simultaneously the selected multiple frame images.

15. The method of claim 14, wherein the displaying of the at least one of the plurality of frame images, each of which has the motion blur factor equal to or less than the threshold value and is obtained prior to the select instruction input time, displays the motion blur factors of the multiple frame images being simultaneously displayed in association with the multiple frame images.

16. The method of claim 14, further comprising the step of:
receiving a select instruction for selecting one among the multiple frame images being simultaneously displayed; and
magnifying and displaying a selected frame image when the select instruction is input to select one among the multiple frame images being simultaneously displayed.

17. The method of claim 10, further comprising the step of:
displaying information related to a motion blur factor of the selected frame image when the motion blur factor of the selected frame image exceeds the threshold value.

18. The method of claim 10, wherein the displaying sequentially of the plurality of frame images generated based on the ultrasonic signals includes the steps of:
obtaining the ultrasonic signals containing information of a target object in real time;
generating the plurality of frame images in real time based on the ultrasonic signals obtained in real time;
displaying sequentially the plurality of frame images generated in real time; and
storing at least one among the plurality of frame images generated in real time,
wherein the storing of the at least one among the plurality of frame images generated in real time stores frame images, each of which has a motion blur factor equal to or less than the threshold value, among the plurality of frame images generated in real time.

* * * * *